United States Patent
Embrechts et al.

(10) Patent No.: US 11,971,970 B2
(45) Date of Patent: Apr. 30, 2024

(54) CONCEPT FOR AUTHENTICATING A USER OF A MOBILE DEVICE

(71) Applicant: Sony Group Corporation, Tokyo (JP)

(72) Inventors: Hugo Embrechts, Stuttgart (DE); Gonzalo Bailador Del Pozo, Stuttgart (DE); Dimitri Torfs, Stuttgart (DE)

(73) Assignee: SONY GROUP CORPORATION, Tokyo (JP)

( * ) Notice: Subject to any disclaimer, the term of this patent is extended or adjusted under 35 U.S.C. 154(b) by 311 days.

(21) Appl. No.: 17/437,045

(22) PCT Filed: Feb. 26, 2020

(86) PCT No.: PCT/EP2020/055063
§ 371 (c)(1),
(2) Date: Sep. 8, 2021

(87) PCT Pub. No.: WO2020/187542
PCT Pub. Date: Sep. 24, 2020

(65) Prior Publication Data
US 2022/0179933 A1 Jun. 9, 2022

(30) Foreign Application Priority Data
Mar. 15, 2019 (EP) ..................... 19163173

(51) Int. Cl.
*G06F 21/32* (2013.01)
*A61B 5/11* (2006.01)
(Continued)

(52) U.S. Cl.
CPC .............. *G06F 21/32* (2013.01); *A61B 5/112* (2013.01); *A61B 5/117* (2013.01); *G06N 20/10* (2019.01); *G06V 10/82* (2022.01); *G06V 40/25* (2022.01)

(58) Field of Classification Search
CPC ........ G06F 21/32; G06N 20/10; G06V 40/25; A61B 5/112; A61B 5/117
See application file for complete search history.

(56) References Cited

U.S. PATENT DOCUMENTS 8,856,888 B2   10/2014   Yamada
10,231,651 B2   3/2019   Deng et al.
(Continued)

OTHER PUBLICATIONS

International Search Report and Written Opinion dated Mar. 31, 2020, received for PCT Application PCT/EP2020/055063, Filed on Feb. 26, 2020, 9 pages.
(Continued)

*Primary Examiner* — Thaddeus J Plecha
(74) *Attorney, Agent, or Firm* — XSENSUS LLP (57) ABSTRACT

The present disclosure generally relates to authenticating a user of a mobile device based on motion data of said mobile device. Embodiments provide a method, apparatus and computer program for authenticating a user, a mobile device comprising such an apparatus and a system. The method comprises detecting an outfit of the user. The method comprises analyzing a gait of the user using a machine-learning model using motion data of a mobile device as input to the machine-learning model. The analysis is based on the identified outfit of the user. The method comprises authenticating the user based on the analysis of the gait of the user.

20 Claims, 4 Drawing Sheets

(51) Int. Cl.
    *A61B 5/117*     (2016.01)
    *G06N 20/10*     (2019.01)
    *G06V 10/82*     (2022.01)
    *G06V 40/20*     (2022.01)

(56) References Cited

U.S. PATENT DOCUMENTS

| | | | |
|---|---|---|---|
| 11,402,971 B1 * | 8/2022 | McNamara | G06V 40/103 |
| 2015/0230734 A1 | 8/2015 | Cheung | |
| 2016/0307031 A1 | 10/2016 | Zhong et al. | |
| 2017/0109514 A1 | 4/2017 | Cheng et al. | |
| 2018/0078179 A1 | 3/2018 | Deng et al. | |
| 2018/0089408 A1 * | 3/2018 | Cheung | G06F 21/32 |
| 2021/0224524 A1 * | 7/2021 | Liu | G06F 18/214 |

OTHER PUBLICATIONS

Shrestha et al., "Walk-Unlock: Zero-Interaction Authentication Protected with Multi-Modal Gait Biometrics", Arxiv.Org., Cornell University Library, arXiv: 160500766v1, May 3, 2016, pp. 1-20.

Cattin, "Biometric Authentication System Using Human Gait", Dissertation submitted to the Swiss Federal Institute of Technology, Diss. ETH No. 14603, 2002, pp. 1-124.

Google, "Set your Android Device to Automatically Unlock", Android Help, Available Online at: https://support.google.com/android/answer/9075927?hl=en, 2018, pp. 1-3.

* cited by examiner

CONCEPT FOR AUTHENTICATING A USER OF A MOBILE DEVICE

CROSS-REFERENCE TO RELATED APPLICATIONS

The present application is based on PCT filing PCT/EP2020/055063, filed Feb. 26, 2020, which claims priority to EP 19163173.8, filed Mar. 15, 2019, the entire contents of each are incorporated herein by reference.

FIELD

The present disclosure generally relates to authenticating a user of a mobile device based on motion data of said mobile device.

BACKGROUND

To access a restricted resource, a user often has to authenticate him- or herself towards the resource, e.g. to enable a gatekeeper of said resource to determine, whether the user is to be granted access to the resource. There are many ways of authenticating user, such as e.g. physical keys, passwords, biometric scanners etc. For example, the user may use the physical key to open a door or cabinet, or the user may enter a password to log onto a computer. One way of authenticating a user is based on an analysis of a gait of the user.

SUMMARY

It is an object of the present disclosure to provide a method, an apparatus and a computer program for authenticating a user, a mobile device comprising such an apparatus or executing such a method, and a corresponding system that enable an improved authentication of a user based on the gait of the user.

Embodiments of the present disclosure provide a method for authenticating a user. The method comprises detecting an outfit of the user. The method comprises analyzing a gait of the user using a machine-learning model using motion data of a mobile device as input to the machine-learning model. The analysis is based on the identified outfit of the user. The method comprises authenticating the user based on the analysis of the gait of the user.

Embodiments of the present disclosure provide a computer program having a program code for performing a method for authenticating a user, when the computer program is executed on a computer, a processor, or a programmable hardware component. The method comprises detecting an outfit of the user. The method comprises analyzing a gait of the user using a machine-learning model using motion data of a mobile device as input to the machine-learning model. The analysis is based on the identified outfit of the user. The method comprises authenticating the user based on the analysis of the gait of the user.

Embodiments of the present disclosure provide an apparatus for authenticating a user. The apparatus comprises circuitry configured to obtain motion data from a sensor of a mobile device. The circuitry is configured to detect an outfit of the user. The circuitry is configured to analyze a gait of the user using a machine-learning model. The motion data is used as input to the machine-learning model. The analysis is based on the identified outfit of the user. The circuitry is configured to authenticate the user based on the analysis of the gait of the user.

Embodiments of the present disclosure provide a mobile device comprising an apparatus for authenticating a user. The apparatus comprises circuitry configured to obtain motion data from a sensor of a mobile device. The circuitry is configured to detect an outfit of the user. The circuitry is configured to analyze a gait of the user using a machine-learning model. The motion data is used as input to the machine-learning model. The analysis is based on the identified outfit of the user. The circuitry is configured to authenticate the user based on the analysis of the gait of the user.

Embodiments of the present disclosure provide a system comprising a transmitter device and a mobile device comprising an apparatus for authenticating a user. The transmitter device is suitable for being attached to a component of an outfit. The transmitter device is configured to transmit a radio-frequency signal to the mobile device. The mobile device is configured to authenticate a user based on the transmitted radio-frequency signal.

BRIEF DESCRIPTION OF THE FIGURES

Some examples of apparatuses and/or methods will be described in the following by way of example only, and with reference to the accompanying figures, in which.

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1A:
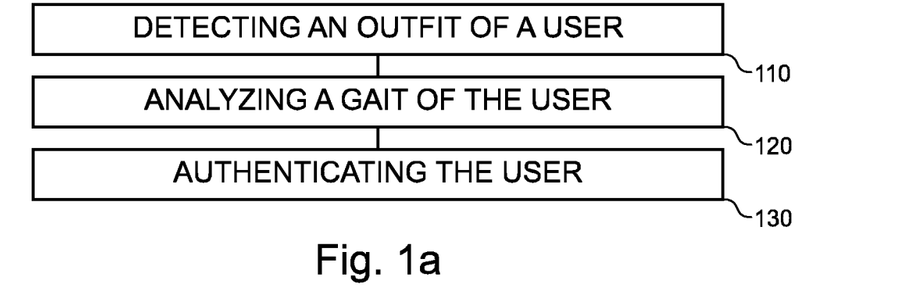
FIGS. 1a and 1b show flow charts of embodiments of a method for authenticating a user.
Figure 1B:
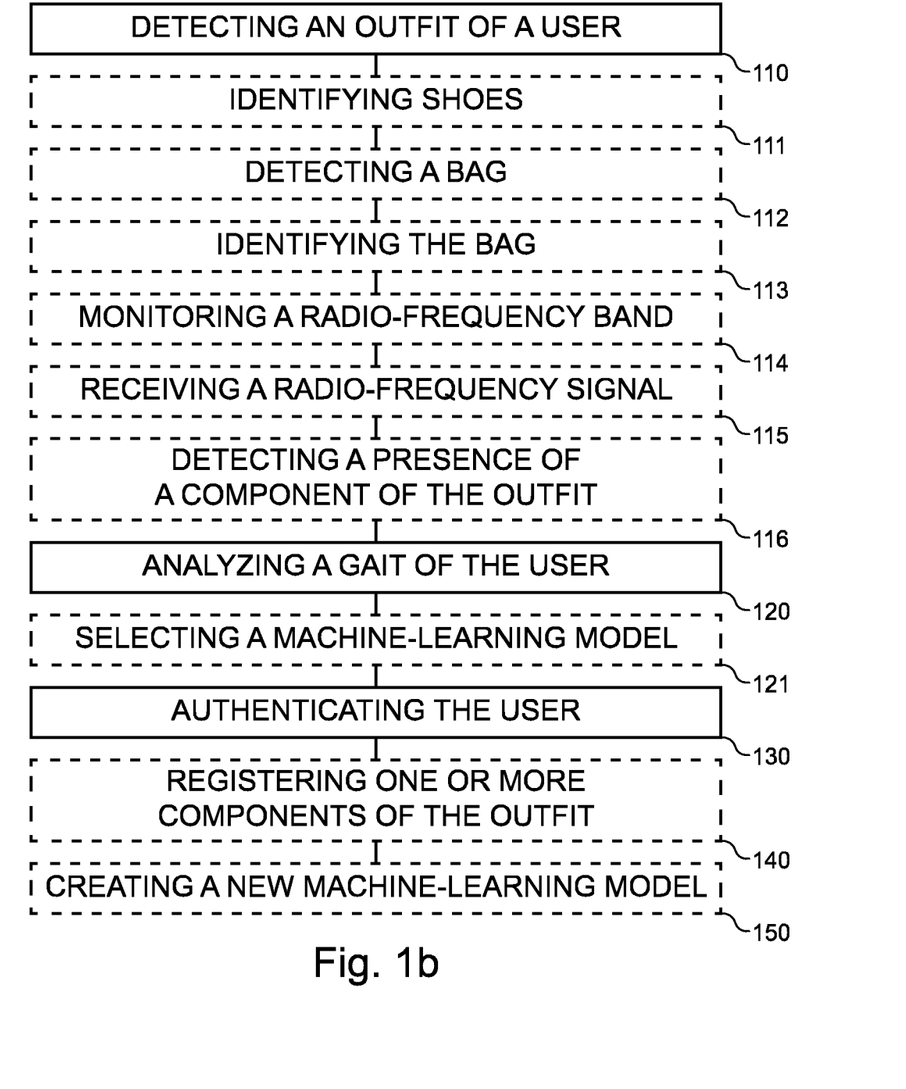

FIGS. 1a and 1b show flow charts of embodiments of a method for authenticating a user. The method comprises detecting 110 an outfit of the user. The method comprises analyzing 120 a gait of the user using a machine-learning model using motion data of a mobile device as input to the machine-learning model. The analysis is based on the identified outfit of the user. The method comprises authenticating 130 the user based on the analysis of the gait of the user. The method may be executed by the mobile device 100.

Figure 1C:
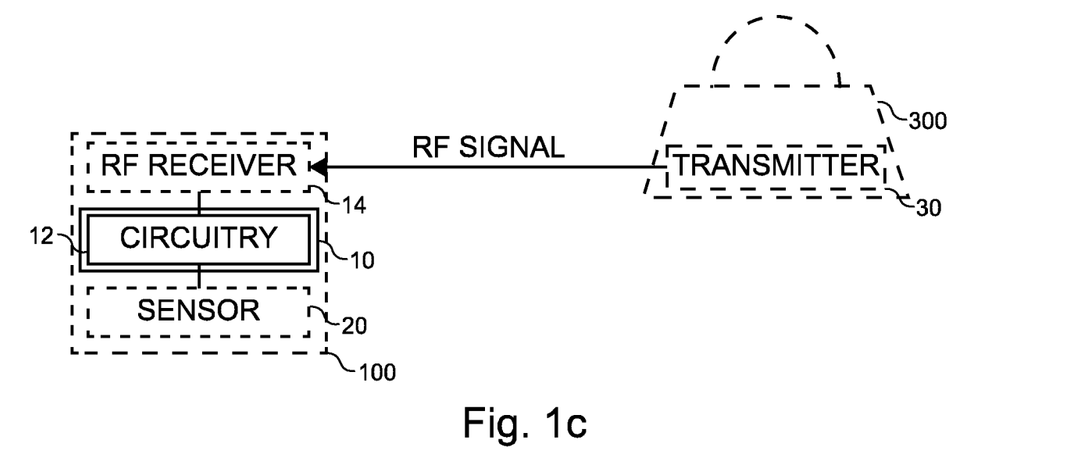
FIG. 1c shows a block diagram of an apparatus for authenticating a user, of a mobile device comprising an apparatus for authenticating a user, and of a system comprising a transmitter device and a mobile device comprising an apparatus for authenticating a user.

FIG. 1c shows a block diagram of a (corresponding) apparatus 10 for authenticating a user. The apparatus 10 comprises circuitry 12. For example, the circuitry 12 may be configured to execute the method introduced in connection with FIGS. 1a and/or 1b. For example, the circuitry 12 is configured to obtain motion data from a sensor 20 of a mobile device 100. The circuitry 12 is configured to detect an outfit of the user. The circuitry 12 is configured to analyze a gait of the user using a machine-learning model. The motion data is used as input to the machine-learning model. The analysis is based on the identified outfit of the user. The circuitry is configured to authenticate the user based on the analysis of the gait of the user. FIG. 1c further shows the mobile device 100 comprising the apparatus 10. The mobile device 100 further comprises the sensor 20. FIG. 1c further shows a system 1000 comprising the mobile device 100 (with the apparatus 10) and a transmitter device 30.

The following description relates both to the method of FIGS. 1a and/or 1b and to the apparatus 10, the mobile device 100 and the system 1000 of FIG. 1c.

At least some embodiments of the present disclosure relate to a method, apparatus and computer program for authenticating a user based on an analysis of the gait (i.e. a manner of walking) of the user. The gait of the user may change depending on the circumstances, e.g. depending on a condition of the road or depending on other people impeding the user walking. One other major factor that influences the gait of the user is the outfit that the user is wearing or carrying. For example, the user may walk differently in different types of shoes, e.g. walk differently in formal footwear compared to beach shoes, or walk differently in high heeled-shoes than compared to trainers. Another major factor may be a bag that is worn or carried by the user. For example, if the user wears a (heavy) backpack, his or her gait may have less spring; if the user carries a handbag over a shoulder or a travel bag in the hand, the walk may be slightly lopsided, causing changes to the gait of the user. Furthermore, the user may walk differently in heavy jeans than in a skirt or in bathing shorts. Embodiments may thus detect the outfit of the user and use this outfit of the user in the analysis of the gait, e.g. by selecting an appropriate machine-learning model, or by using the detected outfit as an input to a single machine-learning model.

At least some embodiments are performed by the mobile device 100. For example, the mobile device may be a mobile personal computing device, such as a smartphone, a tablet computer or a laptop computer. Alternatively, the mobile device may be wearable device, such as a smartwatch, a fitness tracker, a cardio tracking device, smart glasses or smart jewelry.

The method comprises detecting 110 the outfit of the user. In embodiments, the outfit may e.g. comprise a bag that is worn and/or carried by the user, and/or shoes that are worn by the user. In more general terms, the outfit may comprise one or more components (i.e. outfit components). For example, the one or more components of the outfit may comprise at least one of shoes worn by the user, a bag worn or carried by the user, and a set of trousers, skirt or legwear worn by the user. For example, the detecting 110 of the outfit of the user may comprise at least one of identifying shoes worn by the user, detecting a bag worn or carried by the user, and identifying trousers, skirt or legwear worn by the user. The worn shoes, the worn trousers and a worn or carried bag may influence the gait of the user. Consequently, an accuracy of the authentication may be improved by identifying the shoes and/or trousers and detecting the bag.

In at least some embodiments, the method comprises identifying 111 shoes worn by the user. For example, the identifying 111 if the shoes worn by the user may comprise identifying a type of the shoes worn by the user, i.e. whether the shoes are trainers, beachwear, formal shoes, high-heeled shoes etc. Additionally or alternatively, the identifying 111 if the shoes worn by the user may comprise identifying specific shoes worn by the user, e.g. after the specific shoes are registered with the apparatus or the entity performing the method, such as the mobile device.

In various embodiments, the detecting 110 of the outfit may comprise detecting 112 a bag worn or carried by the user. For example, the detecting 112 of the bag may comprise identifying the type or location of the bag, i.e. whether the bag is a backpack that is worn by the user on his/her back or whether the bag is a handbag, sling bag or suitcase that is carried by the user over a shoulder or in a hand of the user. In these cases, the back of the user, shoulder and the hand of the user may be the location of the bag, and the types "backpack", "handbag", "sling bag" or "suitcase" may be the type of the bag. In some embodiments, the detecting 112 of the bag may comprise identifying 113 a specific bag, e.g. after the specific bag is registered with the apparatus or the entity performing the method, such as the mobile device.

The outfit may be detected using various means. For example, at least a part of the outfit may be detected based on a radio-frequency signal emitted by a component of the outfit. Radio frequency (RF) is an oscillation rate of an alternating electric current or voltage or of an electric or electromagnetic field in the frequency range from around 20 kHz to around 300 GHz. For example, the radio-frequency signal may be a wireless radio-frequency signal. For example, the circuitry 12 may comprise a processing circuitry, such as a processor, and (optionally) interface circuitry. For example, the interface circuitry may be coupled to a radio-frequency receiver 14 of the mobile device. In other words, the mobile device 100 may comprise the radio-frequency receiver 14 that is coupled to the circuitry 12. The radio-frequency signal may be received via the radio-frequency receiver 14 of the mobile device 100. The user may be authenticated based on the transmitted radio-frequency signal. In other words, the mobile device may be configured to authenticate the user based on the transmitted radio-frequency signal. The circuitry 12 may be configured to obtain a radio-frequency signal from a transmitter device 30 of a component 300, of the outfit. The radio-frequency signal may be used in the detection of the outfit.

In at least some embodiments, the radio-frequency signal may be a near-field communication (NFC)-based radio-frequency signal. Accordingly, the radio-frequency receiver may be or comprise a NFC receiver. Alternatively, the radio-frequency signal may be a Bluetooth-based radio-frequency signal. Accordingly, the radio-frequency receiver may be or comprise a Bluetooth receiver. In some cases, the radio-frequency signal may be a Radio Frequency Identification (RFID)-based radio frequency signal. Accordingly, the radio-frequency receiver may be or comprise an RFID receiver or reader. In some embodiments, more than one radio-frequency signal using more than one radio-frequency technology may be used.

For example, the transmitter device may be suitable for being attached to a component of the outfit. For example, the transmitter device may be permanently attached to the component of the outfit, e.g. sewn into the component of the outfit, glued to the component of the outfit or stapled to the component of the outfit. Alternatively, the transmitter device may be removably attached to the component of the outfit, e.g. via a clip or a snap fastener. The transmitter device may be configured to transmit the radio-frequency signal to the mobile device. For example, the transmitter device may be one of an NFC beacon, a Bluetooth beacon or an RFID tag.

The method may comprise monitoring 114 a radio-frequency band to detect the outfit of the user. For example, the radio-frequency band may be monitored 114 to determine whether the user wears or carries a bag, to identify the bag, or to identify shoes worn by the user. By monitoring the radio-frequency band, a radio-frequency signal that is transmitted by a transmitter device of a component of the outfit may be detected and received. Using the received radio-frequency signal, the component of the outfit may be detected or identified.

In at least some embodiments, the method may comprise detecting 116 a presence of a component of the outfit. For example, the outfit may comprise one or more components. By detecting the presence of each of the one or more components of the outfit, the outfit may be detected. For example, the method may comprise receiving 115 a radio-frequency signal from a transmitter device of the component of the outfit. The method may comprise detecting the presence of the component of the outfit based on the radio-frequency signal. In other words, a radio-frequency signal that is received from the component of the outfit may indicate the presence of the component of the outfit. The radio-frequency signal may enable the detection of the presence of the component, and may thus enable detecting the outfit. For example, the method may comprise determining whether the user (presently) wears or carries a bag based on the received radio-frequency signal. For example, the determination, whether the user (presently) wears or carries a bag may be positive if a radio-frequency signal is received from a bag, and negative otherwise.

Additionally, the method may comprise determining a type or a specific item of the component of the outfit based on the received radio-frequency signal, e.g. identifying the bag or the shoes worn by the user. For example, the radio-frequency signal may comprise identification information (e.g. one or more identifiers) of the one or more components of the outfit. The type or the specific item of the component of the outfit may be determined based on the identification information of the one or more components of the outfit. For example, the identification information may be registered 140 with the apparatus 10 or with the entity executing the method, e.g. the mobile device 100. The method may comprise determining the type or specific item of the component based on the registered identification information. In other words, the bag or the shoes may be identified based on the registered identification information and based on the identification information received in the radio-frequency signal. The same identification information may be used to detect the presence of the components of the outfit (e.g. by comparing an identifier received with the radio-frequency signal to the registered identification information).

Alternatively or additionally, the detection 110 of the outfit may be based on a further ma-chine-learning model. The motion data of the mobile device being may be used as input to the machine-learning model. This may enable a detection of the outfit if the components of the outfit are not equipped with a transmitter device.

The method comprises analyzing 120 the gait of the user using a machine-learning model using motion data of a mobile device as input to the machine-learning model.

Machine learning refers to algorithms and statistical models that computer systems may use to perform a specific task without using explicit instructions, instead relying on models and inference. For example, in machine learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and associated training content information, the machine-learning model "learns" to recognize the content of the images, so the content of images that are not included of the training images can be recognized using the machine-learning model. The same principle may be used for other kinds of sensor data as well, such as the motion data in embodiments: By training a machine-learning model using training sensor data and a desired output, the machine-learning model "learns" a transformation between the sensor data and the output, which can be used to provide an output based on non-training sensor data provided to the machine-learning model.

Machine-learning models are trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the t samples provided during the training. In embodiments, the machine-learning model may be trained using the motion data of the mobile device 100 as training input, and using a (binary) training output that indicates whether the authentication is successful or a training output indicating a confidence value of the authentication as training output. For example, the further machine-learning model may be trained using the motion data of the mobile device 100 as training input and the outfit, e.g. the components of the outfit, as training output.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge, e.g. based on the training performed by the machine-learning algorithm. In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of the sum of its inputs. The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine. Support vector machines (i.e. support vector networks) are supervised learning models with associated learning algorithms that may be used to analyze data, e.g. in classification or regression analysis. Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

In embodiments, the machine-learning model may be used to determine, using the motion data as input to the machine-learning model, whether a person carrying or wearing the mobile device is the user the machine-learning model is trained on. In other words, the machine-learning model may be used to determine a match or correspondence between a gait of a person carrying or wearing the mobile device (leading to motion data that is based on the gait of the user carrying or wearing the mobile device) and a gait of the user the machine-learning model is trained on.

The motion data is used as input to the machine-learning model. For example, the motion data may comprise or be based on at least one of accelerometer data, barometric data, gyroscope data and compass data. The motion data may indicate a movement of the mobile device that is caused by the gait of the user, e.g. that is caused by the user walking. For example, the motion data may be provided by a sensor 20 of the mobile device 100. The sensor 20 may correspond to or comprise at least one of a motion sensor, an accelerometer, a barometric sensor, a gyroscope and a compass. The sensor 20 is coupled to the circuitry 12, e.g. via interface circuitry of the circuitry 12.

The analysis is based on the identified outfit of the user. For example, the machine-learning model may be selected from a plurality of machine-learning models based on the detected outfit, or the detected outfit may be used as input to the machine-learning model.

In at least some embodiments, the method comprises selecting 121, based on the detected outfit, a machine-learning model out of a plurality of machine-learning models. The analysis of the gait may be based on the selected machine-learning model. Each of the plurality of machine-learning models may be provided for a different outfit of the user. In other words, for each of the plurality of different possible outfits of the user, a specific machine-learning model may be created and/or trained. The method may comprise creating and/or training a specific machine-learning model for each of the plurality of different possible outfits of the user. By using specialized machine-learning models based on the different outfits, the models may be separately trained and may thus provide more accurate authentication results for a specific outfit.

In embodiments, the plurality of machine-learning models may be provided using different granularities. In some embodiments, a granularity that is limited to a type of the components of the outfit may be used. For example, in embodiments in which the outfit comprises shoes and optionally a bag, the plurality of machine-learning models may be provided for a type of shoes (e.g. formal shoes, beach shoes, trainers, high-heeled shoes) without a bag or for a combination of a type of shoe and a type of bag (a backpack, a handbag, a sling bag, a suitcase).

In other words, the plurality of machine-learning models may be based on a combination of different types of shoes and different types of bags (or no bag). Alternatively, a higher granularity may be used. In some embodiments, a granularity that is based on a combination of specific components of the outfit may be used. For example, in embodiments in which the outfit comprises shoes and optionally a bag, the plurality of machine-learning models may be provided for specific shoes (e.g. as registered 140 by the user) without a bag or for a combination of specific shoes and a specific bag (e.g. as registered 140 by the user). In both granularities, the presence of a bag may be used as a selection criterion in the selection 121 of the machine-learning model. The method may comprise selecting the machine-learning model based on the detected bag, e.g. by selecting the machine-learning model from a first subset of the plurality of machine-learning models if no bag is detected, and by selecting the machine-learning model from a second subset of the plurality of machine-learning models if a bag is detected.

For example, the detecting 110 of the outfit of the user may comprise identifying 111 the shoes worn by the user, detecting 112 a bag worn or carried by the user (or not), and/or identifying 113 the bag worn or carried by the user. The method may comprise selecting 121 the machine-learning model based on a type of the shoes or based on specific shoes owned by the user. For example, the plurality of machine-learning models may be based on a plurality of different types of shoes or based on a plurality of specific shoes owned by the user. The selecting of the machine-learning model may comprise selecting a machine-learning model of the plurality of machine-learning models that matches a type of shoe or a specific shoe identified 111 in the detection 110 of the outfit of the user. By selecting the machine-learning model based on the type of the shoes, a number of machine-learning models required may be reduced. By selecting the machine-learning model based on specific shoes owned by the user, a higher accuracy may be reached. The method may comprise selecting 121 the machine-learning model based on a type of the bag or based on a specific bag owned by the user. For example, the plurality of machine-learning models may be based on a plurality of different types of bags (or locations of bags) or based on a plurality of specific bags owned by the user. The selecting of the machine-learning model may comprise selecting a machine-learning model of the plurality of machine-learning models that matches a type of bag (or a location of the bag) or a specific bag identified 113 in the detection 110 of the outfit of the user. By selecting the machine-learning model based on the detected and/or identified bag, a more specialized machine-learning model may be selected.

In at least some embodiments, the detected outfit of the user may be used as input to the machine-learning model. For example, the detected outfit of the user may be used as input to the machine-learning model without selecting a specialized machine-learning model. This may enable the use of a single model. Alternatively, the machine-learning model may be selected based on whether or not the user carries a bag, and the detected type or identification of the bag may be used as input to the machine-learning model. In some embodiments, the machine-learning model may be selected based on a detected type of the shoes worn by the user, and the detected identity of the shoes may be used as input to the machine-learning model. In other words, in some embodiments, the machine-learning model may be selected based on a first granularity of the detection of the outfit of the user, and a second granularity of the detection of the outfit of the user may be used as input to the machine-learning model, the second granularity being higher than the first granularity. For example, the method may comprise codifying the outfit of the user to obtain one or more digital values representing the outfit of the user. The one or more digital values may be provided as input values to the machine-learning model. In at least some embodiments, a detected type of shoes worn by the user and/or detected specific shoes of the user may be provided as input to the machine-learning model.

The method comprises authenticating 130 the user based on the analysis of the gait of the user. In embodiments, the authenticating 130 of the user may determine that (or whether) the person using the mobile device is the user (i.e. the user the machine-learning network is trained on). For example, the user may be authenticated such, that the authentication is successful if the person using the mobile device matches the user that the machine-learning model is trained on. The user may be authenticated towards the mobile device, i.e. the authentication may be performed by and valid for the mobile device. For example, if the user is successfully authenticated, the user may be granted access to the mobile device (e.g. by unlocking the mobile device) or given access to a further device or to a service. In other words, the method may comprise unlocking the mobile device based on the authentication of the user. The method may comprise providing access to the further device or to the service based on the authentication of the user. This may enable the user to use the further device or the service, such as an Automated Teller Machine (ATM), a door or a vehicle. For example, the further device may be an ATM, a door, a computer, another mobile device, a vehicle etc. The further service may be a service that is accessed via the mobile device, e.g. a mobile banking service, an application of a car sharing company or a service for accessing confidential and/or personal messages.

In some embodiments, the authentication may be performed continuously (i.e. periodically in pre-defined time intervals or whenever new motion data is generated) or upon request of the user. For example, the gait of the user may be continuously analyzed 120 using the machine-learning model. In other words, the motion data may be continuously (i.e. periodically or whenever new motion data is generated) provided to the machine-learning model when it is generated. The user may be continuously (i.e. periodically or whenever an output of the machine-learning model changes) authenticated 130 based on the continuous analysis of the gait of the user. This may avoid delays in the authentication of the user and may avoid storing the motion data.

Alternatively, the analysis 120 of the gait of the user may be triggered by a request for authentication. For example, the request for authentication may be triggered by an unlocking procedure of the mobile device, or by a request of an application of the mobile devices, the request indicating that an (additional) authentication of the user is desired or required. The analysis of the gait of the user may be based on accumulated motion data of the mobile device. The accumulated motion data may comprise motion data of a pre-defined time interval (or of a pre-defined amount) prior to the request for authentication. For example, the motion data may be stored or accumulated by a motion processor or motion co-processor of the mobile device. For example, the circuitry 12 may comprise the motion processor or motion co-processor. The pre-defined time interval or amount may be based on a storage capacity of the motion (co-)processor, or the pre-defined time interval or amount may be based on a parameter of the analysis of the gait of the user. This may avoid a continuous analysis of the gait of the user, thus reducing a power consumption of the mobile device.

In some embodiments, the authentication of the user may be further based on the presence of a component of the outfit. For example, the presence of a component of the outfit being detected may provide a further indication that it is actually the user that is being authenticated. In other words, the presence of the component of the outfit may indicate that the user is in possession of the component of the outfit. The method may comprise using the detected presence of the component of the outfit as a second factor in the authentication of the user. For example, a first factor of the authentication may be the analysis of the gait of the user, and the second factor may be detected presence of the component of the outfit. The detected presence of the component of the outfit may both enable the detection of the outfit and a user of the presence as a second factor in a two-factor authentication.

In at least some embodiments, the method may comprise registering 140 the one or more components of the outfit with the mobile device. For example, the one or more components of the outfit comprise shoes (e.g. one or more pairs of shoes) and/or a bag (e.g. one or more bags). For example, the one or more components of the outfit may be registered by receiving radio-frequency signals comprising identification information from transmitter devices of the one or more components, and registering the one or more components of the outfit based on the one or more radio-frequency signals. For example, the identification information may comprise an identification of the component, such as a serial number and/or a model number of the respective component, and/or information on a type of the component, e.g. whether the components are shoes, bags etc. In some embodiments, the identification information may be a generic identification information. For example, the generic identification information may indicate that the transmitter device the generic identification information is received from is a transmitter device that is attachable to any component of the outfit. The user may then associate specific identification information with the generic identification information, e.g. using an application of the mobile device. The association of the specific identification information with the generic identification information may link the generic identification information with the specific identification information, e.g. to indicate that whenever the generic identification information is received, specific shoes that are attached to or a specific bag that is attached to said transmitter device providing the generic identification information are part of the outfit of the user. In embodiment, in which the further machine-learning network is used to detect the outfit of the user, the one or more components of the outfit may be registered manually, e.g. using an application of the mobile device. The method may comprise using the one or more registered components of the outfit to detect the outfit. For example, the identification information received during the registration of the one or more components of the outfit may be used to detect the outfit, e.g. by component the identification information received during the registration with identification information received during the detection of the outfit. By registering the one or more components of the outfit with the mobile device, the method and/or apparatus may be enable to detect the outfit.

In some embodiments, the method may comprise creating 150 a new machine-learning model after registering a component of the outfit. For example, the method may comprise creating 150 one or more new machine-learning models after registering a component of the outfit, e.g. one for each new outfit combination of plurality of different possible outfits. The method may comprise training the new machine-learning model (or the one or more new machine-learning models) based on motion data of the mobile device that is obtained while the user wears or carries the newly registered component of the outfit. This may enable a subsequent selection of the trained machine-learning models for the analysis of the gait. The machine-learning model and/or the plurality of machine-learning models may be continuously refined when a corresponding outfit is worn by the user. For example, the method may comprise continuously training the machine-learning model used for analyzing the gait of the user based on the motion data of the mobile device. This may enable a continuous refinement of the respective machine-learning model.

The circuitry 12, e.g. the processing circuitry, may be implemented using one or more processing units, one or more processing devices, any means for processing, such as a processor, a computer or a programmable hardware component being operable with accordingly adapted software. In other words, the described function of the processing circuitry may as well be implemented in software, which is then executed on one or more programmable hardware components. Such hardware components may comprise a general-purpose processor, a Digital Signal Processor (DSP), a micro-controller, etc. The interface circuitry may correspond to one or more inputs and/or outputs for receiving and/or transmitting information, which may be in digital (bit) values according to a specified code, within a module, between modules or between modules of different entities.

More details and aspects of the method and/or the apparatus 10 are mentioned in connection with the proposed concept or one or more examples described above or below (e.g. FIGS. 2 to 3). The method and/or the apparatus 10 may comprise one or more additional optional features corresponding to one or more aspects of the proposed concept or one or more examples described above or below.

At least some embodiments are based on tuning gait authentication models (e.g. the plurality of machine-learning models) based on the worn shoes and carried bags.

Some use cases are built on continuously authenticating a user. To this effect, gait authentication may be used. Several factors may affect the gait authenticator accuracy. For example, there may be a variability of the gait over different days, different speeds of walking, the carrying of a handbag, backpack etc. and/or the wearing of different shoes. In embodiments, the gait authenticator model may be be tuned for a configuration of different shoes and for carrying a backpack or handbag. Using such a tuning, the gait authenticator accuracy may be increased.

Figure 2:
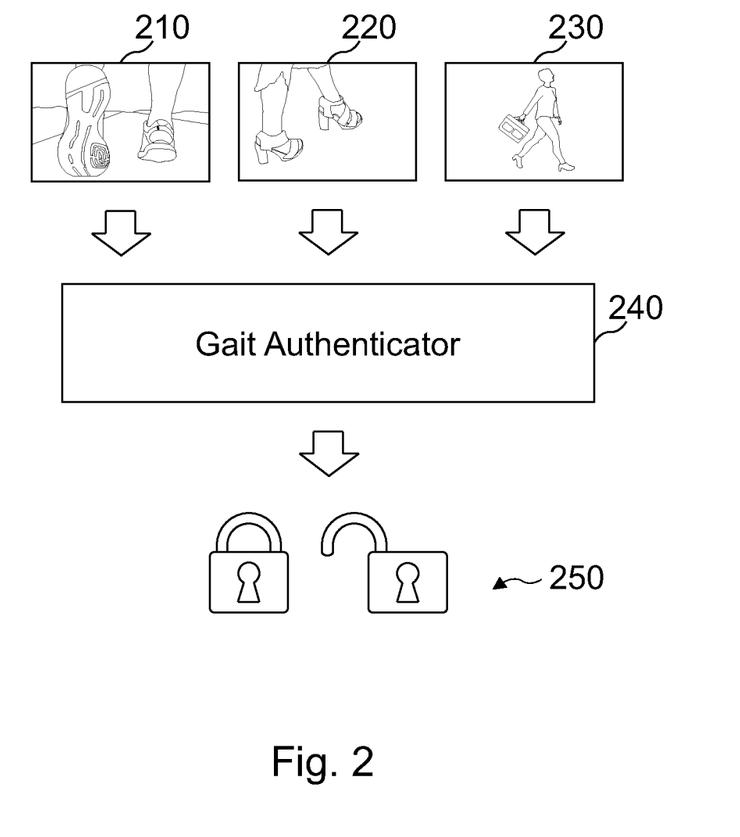
FIG. 2 shows a schematic drawing of a concept for authenticating a user.

FIG. 2 shows a schematic drawing of a concept for authenticating a user. In the concept of FIG. 2, the shoes and/or the bags of a user are used as inputs to a gait authenticator 240. The gait authenticator 240 may be used to unlock 250 something, e.g. the mobile device 100 or another device or service. For example, as shown in FIG. 2 210, trainers of the user may be detected and used as input to the gait authenticator 240, high-heeled shoes may be detected in FIG. 2 220 and used as input to the gait authenticator 240, low-heeled shoes and a bag to be carried may be detected in FIG. 2 230 and used as input to the gait authenticator 240.

At least some embodiments comprise identifying shoes worn by the user and bags carried by the user. During the enrolment (e.g. the registration 140) each worn configuration (e.g. trainers and backpack, as shown in FIG. 3 316) may be identified. Furthermore, a (machine-learning) model may be created and/or tuned (i.e. trained) for each configuration. During the evaluation, the configuration (i.e. the outfit) may be identified (e.g. by detecting 110 the outfit) and a (machine-learning) model may be selected for the configuration. This model may be used to authenticate the user, leading to a usage of a more specific model with expected higher accuracies. Additionally, the possession of the identified shoes or bags may be considered as a second factor of authentication.

Figure 3:
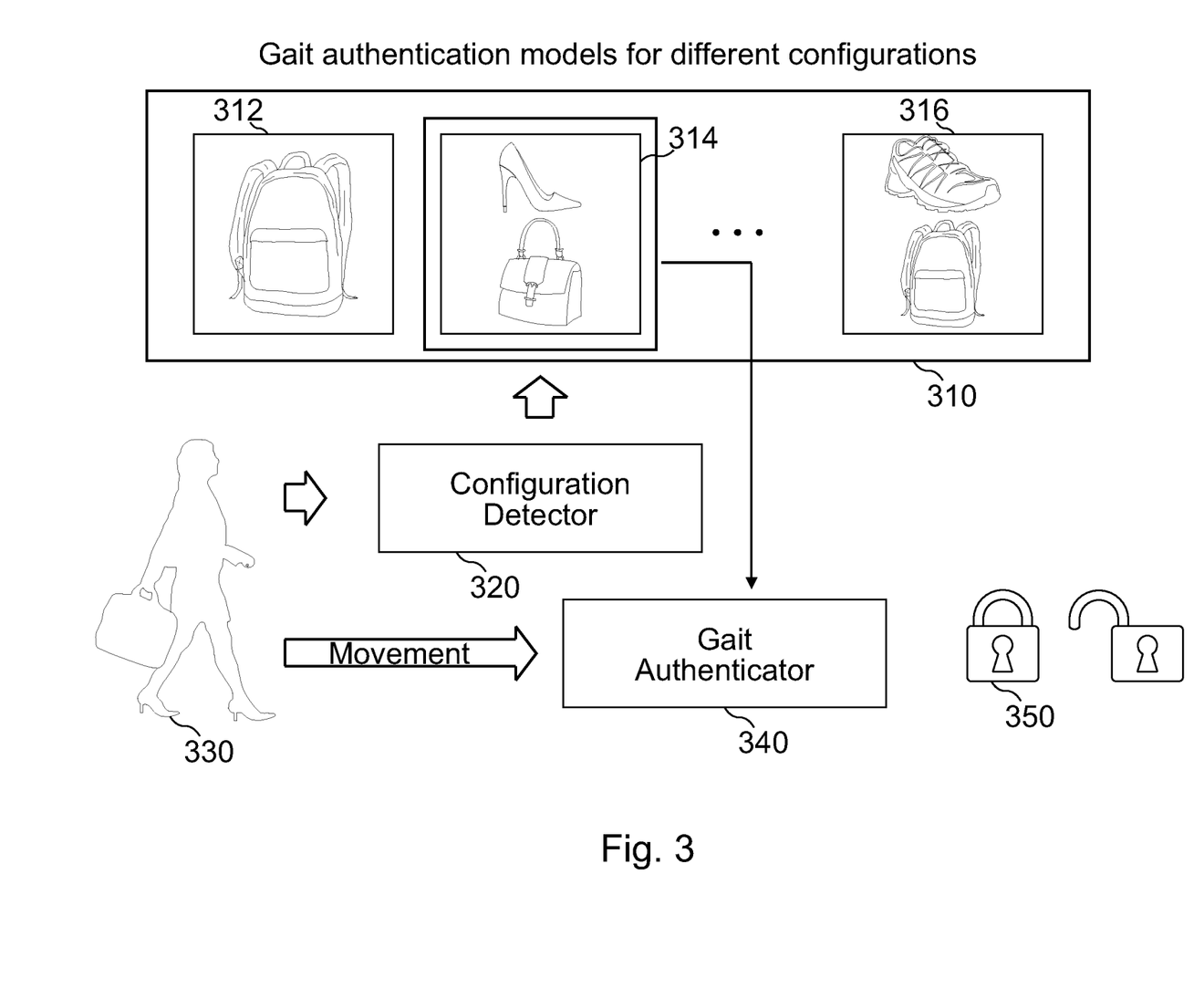
FIG. 3 shows a block diagram of a concept for selecting gait authentication models for different configurations of an outfit.

FIG. 3 shows a block diagram of a concept for selecting gait authentication models for different configurations of an outfit. FIG. 3 shoes gait authentication models for different configurations 310 (e.g. the plurality of machine-learning models), which comprise a first configuration 312 that is based on a backpack, a second configuration 314 that is based on high-heeled shoes and a handbag, and a third configuration 316 that is based on trainers and a light backpack. In FIG. 3, the configuration of user 330 is detected by a configuration detector 320 (e.g. by detecting the outfit 110) and a machine-learning model is selected (in this case the machine-learning model that is based on the second configuration 314) and used by the gait authenticator 340, which is based on a movement (e.g. the motion data) of the user 330. The gait authenticator 340 may be used to unlock 350 something, e.g. the mobile device 100 of the user 330 or another device or service.

Embodiments may be based on a hardware-based approach, e.g. an approach that is based on a tag/beacon (e.g. the transmitter device). The tag/beacon may be attached to the bag or shoes. For example, the tag or beacon may be based on Bluetooth or NFC, and may be detected wirelessly using a smartphone or smartwatch (e.g. the mobile device 100). During enrolment of the shoes/bags, the user may register shoes/bags by approaching them to the smartphone (e.g. the mobile device).

When walking, the authenticator (e.g. the method introduced in connections with FIGS. 1a/1b or apparatus the 10) may train a new model for this configuration. During evaluation, the shoes/bags may be automatically identified by the smartphone (e.g. by detecting the outfit). This could be used as a 2-factor authentication. The gait authenticator may load the specific model for this configuration. Predictions (e.g. the authentication of the used) may be based on this model.

Alternatively or additionally, embodiments may be based on a software-based approach, which may be based on a signal analysis (e.g. of the motion data). No specific hardware may be required). The mobile phone (e.g. the mobile device 100) may analyze the motion data. During enrolment, the user may label the shoes/bags manually to indicate when the user is wearing shoes/bags. When walking, the authenticator may train a new model for this configuration. During evaluation, using machine learning techniques (e.g. the further machine-learning model), an algorithm may automatically detect a type of shoes worn by user and whether the user is carrying any bag. The corresponding configuration may be detected based on the detected type of shoes and based on whether the user is carrying a bag. The gait authenticator may load the specific model for this configuration. Predictions (e.g. the authentication of the used) may be based on this model.

In the hardware-based approach, the shoes/bags may comprise specific hardware, such as Bluetooth or NFC tags (e.g. the transmitter device). The gait authenticator may require pairing the smartphone (e.g. the mobile device) with the shoes/bags. The manual of the gait authenticator may comprise an instruction that the accuracy increases when using specific configurations that are based on the hardware-based NFC/Bluetooth tags.

The following examples pertain to further embodiments:
(1) Method for authenticating a user, the method comprising:
  Detecting an outfit of the user;
  Analyzing a gait of the user using a machine-learning model using motion data of a mobile device as input to the machine-learning model, the analysis being based on the identified outfit of the user;
  Authenticating the user based on the analysis of the gait of the user.
(2) The method according to (1), wherein the detecting of the outfit of the user comprises at least one of identifying shoes worn by the user and detecting a bag worn or carried by the user.
(3) The method according to one of (1) or (2), wherein the method comprises selecting, based on the detected outfit, a machine-learning model out of a plurality of machine-learning models, each of the plurality of machine-learning models being provided for a different outfit of the user and the analysis of the gait being based on the selected machine-learning model.
(4) The method according to (3), wherein for each of a plurality of different possible outfits of the user, a specific machine-learning model is created and/or trained.
(5) The method according to one of (3) or (4), wherein the detecting of the outfit of the user comprises identifying shoes worn by the user, the method comprising selecting the machine-learning model based on a type of the shoes or based on specific shoes owned by the user.
(6) The method according to one of (3) to (5), wherein the detecting of the outfit of the user comprises detecting a bag worn or carried by the user, the method comprising selecting the machine-learning model based on the detected bag.
(7) The method according to one of (5) or (6), further comprising identifying the bag, the method comprising selecting the machine-learning model based on a type of the bag or based on a specific bag owned by the user.
(8) The method according to one of (1) to (7), wherein the detected outfit of the user is used as input to the machine-learning model.
(9) The method according to one of (1) to (8), wherein the method comprises monitoring a radio-frequency band to detect the outfit of the user.
(10) The method according to (9), wherein the radio-frequency band is monitored to determine whether the user wears or carries a bag, to identify the bag, or to identify shoes worn by the user.
(11) The method according to one of (1) to (10), the method comprising detecting a presence of a component of the outfit, the presence of the component of the outfit indicating that the user is in possession of the component of the outfit, the method comprising using the detected presence of the component of the outfit as a second factor in the authentication of the user.
(12) The method according to (11), the method comprising receiving a radio-frequency signal from a transmitter device of the component of the outfit, the method comprising detecting the presence of the component of the outfit based on the radio-frequency signal.
(13) The method according to one of (1) to (12), wherein the detection of the outfit is based on a further machine-learning model, the motion data of the mobile device being used as input to the machine-learning model.
(14) The method according to one of (1) to (13), further comprising registering one or more components of the outfit with the mobile device, the method comprising using the one or more registered components of the outfit to detect the outfit.
(15) The method according to (14), wherein the one or more components of the outfit comprise one or more pairs of shoes and/or one or more bags.
(16) The method according to one of (14) or (15), the method comprising creating a new machine-learning model after registering a component of the outfit, the method comprising training the new machine-learning model based on motion data of the mobile device that is obtained while the user wears or carries the newly registered component of the outfit.
(17) The method according to one of (1) to (16), wherein the method comprises continuously training the machine-learning model used for analyzing the gait of the user based on the motion data of the mobile device.)
(18) The method according to one of (1) to (17), wherein the gait of the user is continuously analyzed using the machine-learning model and the user is continuously authenticated based on the continuous analysis of the gait of the user.
(19) The method according to one of (1) to (17), wherein the analysis (120) of the gait of the user is triggered by a request for authentication, the analysis of the gait of the user being based on accumulated motion data of the mobile device, the accumulated motion data comprising motion data of a pre-defined time interval prior to the request for authentication.

(20) The method according to one of (1) to (19), the method comprising unlocking the mobile device based on the authentication of the user.

(21) The method according to one of (1) to (20), the method comprising providing access to a further device or to a service based on the authentication of the user.)

(22) A computer program having a program code for performing the method according to one of the previous examples, when the computer program is executed on a computer, a processor, or a programmable hardware component.

(23) An apparatus for authenticating a user, the apparatus comprising:
Circuitry configured to:
Obtain motion data from a sensor of a mobile device,
Detect an outfit of the user,
Analyze a gait of the user using a machine-learning model, the motion data being used as input to the machine-learning model, the analysis being based on the identified outfit of the user, and
Authenticate the user based on the analysis of the gait of the user.

(24) The apparatus according to (23), wherein the circuitry is configured to obtain a radio-frequency signal from a transmitter device of a component of the outfit, the radio-frequency signal being used in the detection of the outfit.

(25) A mobile device comprising the apparatus according to one of (23) or (24).

(26) A system comprising the mobile device according to (25) and a transmitter device, the transmitter device being suitable for being attached to a component of an outfit, the transmitter device being configured to transmit a radio-frequency signal to the mobile device, the mobile device being configured to authenticate a user based on the transmitted radio-frequency signal.

The aspects and features mentioned and described together with one or more of the previously detailed examples and figures, may as well be combined with one or more of the other examples in order to replace a like feature of the other example or in order to additionally introduce the feature to the other example.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor or computer readable and encode machine-executable, processor-executable or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further examples may also cover computers, processors or control units programmed to perform the acts of the above-described methods or (field) programmable logic arrays ((F)PLAs) or (field) programmable gate arrays ((F) PGAs), programmed to perform the acts of the above-described methods.

The description and drawings merely illustrate the principles of the disclosure. Furthermore, all examples recited herein are principally intended expressly to be only for illustrative purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

A functional block denoted as "means for . . ." performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a signal", "means for generating a signal.", etc., may be implemented in the form of dedicated hardware, such as "a signal provider", "a signal processing unit", "a processor", "a controller", etc. as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software, but may include digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or steps, respectively. Such sub acts may be included and part of the disclosure of this single act unless explicitly excluded.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

What is claimed is:

1. A method for authenticating a user, the method comprising:
   identifying an outfit of the user;
   analyzing a gait of the user using a machine-learning model using motion data of a mobile device as input to the machine-learning model, the analysis being based on the identified outfit of the user; and
   authenticating the user based on the analysis of the gait of the user.

2. The method according to claim 1, wherein the identifying of the outfit of the user comprises at least one of identifying shoes worn by the user and identifying a bag worn or carried by the user.

3. The method according to claim 1, wherein the method comprises selecting, based on the identified outfit, a machine-learning model out of a plurality of machine-learning models, each of the plurality of machine-learning models being provided for a different outfit of the user and the analysis of the gait being based on the selected machine-learning model.

4. The method according to claim 3, wherein for each of a plurality of different possible outfits of the user, a specific machine-learning model is created and/or trained.

5. The method according to claim 3, wherein the identifying of the outfit of the user comprises identifying shoes worn by the user, the method comprising selecting the machine-learning model based on a type of the shoes or based on specific shoes owned by the user
   and/or wherein the identifying of the outfit of the user comprises identifying a bag worn or carried by the user, the method comprising selecting the machine-learning model based on the identified bag.

6. The method according to claim 5, further comprising identifying the bag, the method comprising selecting the machine-learning model based on a type of the bag or based on a specific bag owned by the user.

7. The method according to claim 1, wherein the identified outfit of the user is used as input to the machine-learning model.

8. The method according to claim 1, wherein the method comprises monitoring a radio-frequency band to identify the outfit of the user.

9. The method according to claim 8, wherein the radio-frequency band is monitored to determine whether the user wears or carries a bag, to identify the bag, or to identify shoes worn by the user.

10. The method according to claim 1, the method comprising detecting a presence of a component of the outfit, the presence of the component of the outfit indicating that the user is in possession of the component of the outfit, the method comprising using the detected presence of the component of the outfit as a second factor in the authentication of the user.

11. The method according to claim 10, the method comprising receiving a radio-frequency signal from a transmitter device of the component of the outfit, the method comprising detecting the presence of the component of the outfit based on the radio-frequency signal.

12. The method according to claim 1, wherein the identification of the outfit is based on a further machine-learning model, the motion data of the mobile device being used as input to the machine-learning model.

13. The method according to claim 1, further comprising registering one or more components of the outfit with the mobile device, the method comprising using the one or more registered components of the outfit to identify the outfit.

14. The method according to claim 13, wherein the one or more components of the outfit comprise one or more pairs of shoes and/or one or more bags.

15. The method according to claim 1, the method comprising creating a new machine-learning model after registering a component of the outfit, the method comprising training the new machine-learning model based on motion data of the mobile device that is obtained while the user wears or carries the newly registered component of the outfit.

16. The method according to claim 1, wherein the gait of the user is continuously analyzed using the machine-learning model and the user is continuously authenticated based on the continuous analysis of the gait of the user
   or wherein the analysis of the gait of the user is triggered by a request for authentication, the analysis of the gait of the user being based on accumulated motion data of the mobile device, the accumulated motion data comprising motion data of a pre-defined time interval prior to the request for authentication.

17. An apparatus for authenticating a user, the apparatus comprising:
   circuitry configured to
      obtain motion data from a sensor of a mobile device;
      identify an outfit of the user;
      analyze a gait of the user using a machine-learning model, the motion data being used as input to the machine-leaning model, the analysis being based on the identified outfit of the user; and
      authenticate the user based on the analysis of the gait of the user.

18. A mobile device comprising the apparatus according to claim 17.

19. A system comprising the mobile device according to claim 18 and a transmitter device, the transmitter device being suitable for being attached to a component of an outfit, the transmitter device being configured to transmit a radio-frequency signal to the mobile device, the mobile device being configured to authenticate a user based on the transmitted radio-frequency signal.

20. One or more non-transitory computer-readable media including computer-program instructions, which when executed by circuitry, cause the circuitry to:
   identify an outfit of the user;
   analyze a gait of the user using a machine-learning model using motion data of a mobile device as input to the machine-learning model, the analysis being based on the identified outfit of the user; and
   authenticate the user based on the analysis of the gait of the user.

* * * * *